(12) United States Patent
Gibbons, Jr.

(10) Patent No.: US 9,918,714 B2
(45) Date of Patent: Mar. 20, 2018

(54) STAPLING DEVICE AND METHOD

(71) Applicant: Cook Medical Technologies LLC, Bloomington, IN (US)

(72) Inventor: William S. Gibbons, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 340 days.

(21) Appl. No.: 14/737,784

(22) Filed: Jun. 12, 2015

(65) Prior Publication Data
US 2015/0359534 A1 Dec. 17, 2015

Related U.S. Application Data

(60) Provisional application No. 62/011,839, filed on Jun. 13, 2014.

(51) Int. Cl.
*A61B 17/08* (2006.01)
*A61B 17/072* (2006.01)
*A61B 17/064* (2006.01)
*A61B 17/00* (2006.01)

(52) U.S. Cl.
CPC .... *A61B 17/07207* (2013.01); *A61B 17/0644* (2013.01); *A61B 17/072* (2013.01); *A61B 2017/00867* (2013.01); *A61B 2017/0645* (2013.01); *A61B 2017/07228* (2013.01); *A61B 2017/07271* (2013.01); *A61B 2217/005* (2013.01)

(58) Field of Classification Search
CPC .......... A61B 17/07207; A61B 17/0682; A61B 2017/0645
See application file for complete search history.

(56) References Cited

U.S. PATENT DOCUMENTS

| | | |
|---|---|---|
| 3,814,104 A | 6/1974 | Irnich et al. |
| 3,869,957 A | 3/1975 | Barth et al. |
| 4,407,286 A | 10/1983 | Noiles et al. |
| 4,448,194 A | 5/1984 | DiGiovanni et al. |
| 4,485,816 A | 12/1984 | Krumme |
| 4,749,114 A | 6/1988 | Green |
| 4,773,420 A | 9/1988 | Green |
| 4,821,939 A | 4/1989 | Green |

(Continued)

FOREIGN PATENT DOCUMENTS

WO 01/58363 A1 8/2001

*Primary Examiner* — Ashley Fishback
(74) *Attorney, Agent, or Firm* — Brinks Gilson & Lione

(57) ABSTRACT

Medical devices and related methods for closing a perforation in a bodily wall are provided. The medical device generally includes an introducer device having a base defining a plurality of recesses formed therein. Visceral staples are disposed within the recesses in a delivery state and are biased toward a deployed state. A holding mechanism retains the staples in the delivery state, and the holding mechanism is moveable relative to the base to allow the staples to extend out of the recesses. The biased nature of the staples will cause them to transition into the deployed state after the staples have been released, such that the staples will thereby pierce adjacent tissue and remain closed. The holding mechanism can be retractable or pivotable out of engagement with the staples. The introducer device can include upper and lower jaws or a slidable cover relative to the base.

20 Claims, 7 Drawing Sheets

(56) References Cited

U.S. PATENT DOCUMENTS

| | | | |
|---|---|---|---|
| 5,192,303 A | 3/1993 | Gatturna et al. | |
| 5,304,204 A * | 4/1994 | Bregen | A61B 17/0644 411/457 |
| 5,318,221 A | 6/1994 | Green et al. | |
| 5,324,307 A | 6/1994 | Jarrett et al. | |
| 5,368,599 A | 11/1994 | Hirsch et al. | |
| 5,395,381 A | 3/1995 | Green et al. | |
| 5,403,329 A | 4/1995 | Hinchcliffe | |
| 5,403,342 A | 4/1995 | Tovey et al. | |
| 5,405,072 A | 4/1995 | Zlock et al. | |
| 5,411,522 A | 5/1995 | Trott | |
| 5,484,451 A | 1/1996 | Akopov et al. | |
| 5,573,543 A | 11/1996 | Akopov et al. | |
| 5,667,527 A | 9/1997 | Cook | |
| 5,984,949 A | 11/1999 | Levin | |
| 6,228,055 B1 | 5/2001 | Foerster et al. | |
| 6,582,452 B2 | 6/2003 | Coleman et al. | |
| 6,652,545 B2 | 11/2003 | Shipp et al. | |
| 6,926,731 B2 | 8/2005 | Coleman et al. | |
| 7,059,508 B2 | 6/2006 | Shelton, IV et al. | |
| 7,060,084 B1 | 6/2006 | Loshakove et al. | |
| RE39,841 E | 9/2007 | Bilotti et al. | |
| 7,326,231 B2 | 2/2008 | Phillips et al. | |
| RE40,237 E | 4/2008 | Bilotti et al. | |
| 7,357,287 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,410,086 B2 | 8/2008 | Ortiz et al. | |
| 7,416,101 B2 | 8/2008 | Shelton, IV et al. | |
| D576,278 S | 9/2008 | Nalagatla et al. | |
| 7,419,080 B2 | 9/2008 | Smith et al. | |
| 7,422,139 B2 | 9/2008 | Shelton, IV et al. | |
| 7,451,904 B2 | 11/2008 | Shelton, IV | |
| 7,455,208 B2 | 11/2008 | Wales et al. | |
| 7,780,685 B2 | 8/2010 | Hunt et al. | |
| 7,794,475 B2 | 9/2010 | Hess et al. | |
| 7,815,652 B2 | 10/2010 | Messerly et al. | |
| 8,177,836 B2 * | 5/2012 | Lee | A61B 17/068 623/2.11 |
| 2004/0087985 A1 | 5/2004 | Loshakove et al. | |
| 2004/0167539 A1 | 8/2004 | Kuehn et al. | |
| 2006/0190016 A1 | 8/2006 | Onuki et al. | |
| 2006/0237023 A1 | 10/2006 | Cox et al. | |
| 2008/0027272 A1 | 1/2008 | Kadykowski | |
| 2008/0097489 A1 | 4/2008 | Goldfarb et al. | |
| 2008/0114380 A1 | 5/2008 | Takemoto et al. | |
| 2008/0114398 A1 | 5/2008 | Phillips et al. | |
| 2008/0140095 A1 | 6/2008 | Smith et al. | |
| 2008/0147116 A1 | 6/2008 | Smith et al. | |
| 2008/0228199 A1 | 9/2008 | Cropper et al. | |
| 2008/0228202 A1 | 9/2008 | Cropper et al. | |
| 2008/0228203 A1 | 9/2008 | Bell et al. | |
| 2008/0234703 A1 | 9/2008 | Cropper et al. | |
| 2008/0234705 A1 | 9/2008 | Cropper et al. | |
| 2008/0255427 A1 | 10/2008 | Satake et al. | |
| 2008/0269566 A1 | 10/2008 | Measamer | |
| 2008/0294178 A1 | 11/2008 | Kortenbach et al. | |
| 2008/0296344 A1 | 12/2008 | Cropper et al. | |
| 2008/0300547 A1 | 12/2008 | Bakos | |
| 2008/0300608 A1 | 12/2008 | Measamer | |
| 2008/0300624 A1 | 12/2008 | Schwemberger et al. | |
| 2009/0318936 A1 | 12/2009 | Harris et al. | |
| 2010/0256634 A1 | 10/2010 | Voegele et al. | |

* cited by examiner

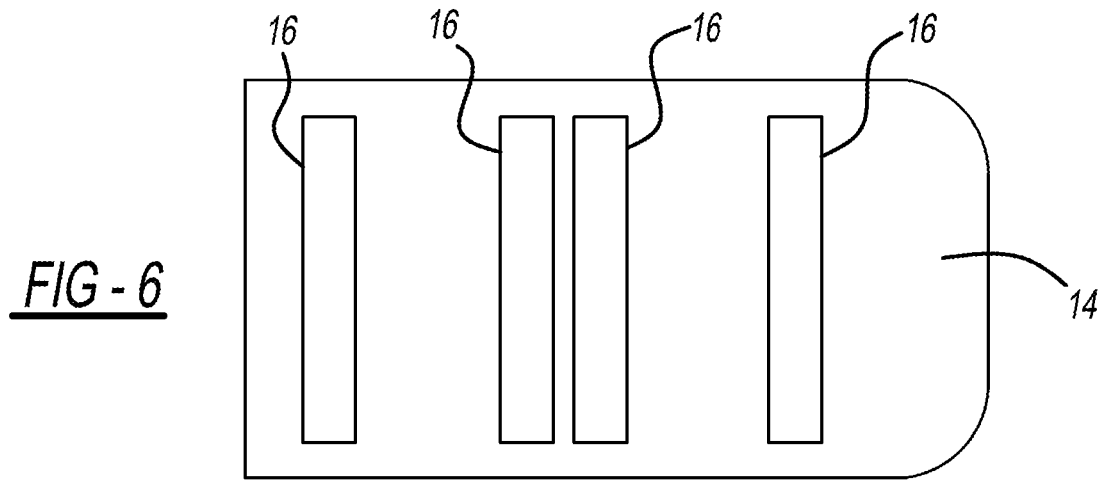
FIG - 6
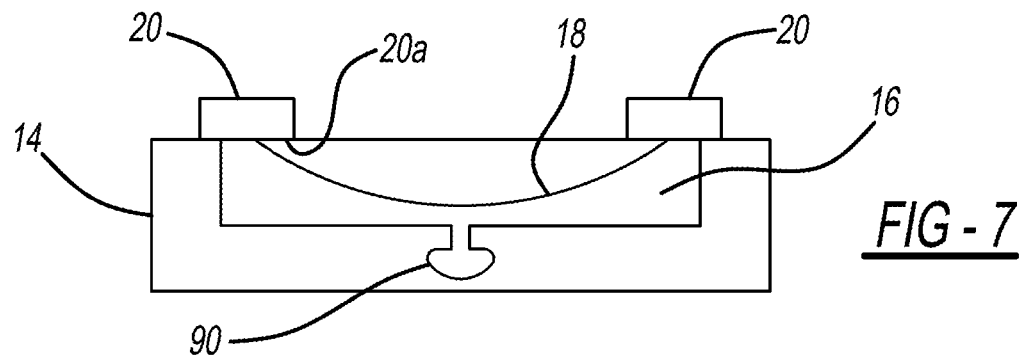
FIG - 7
FIG - 8
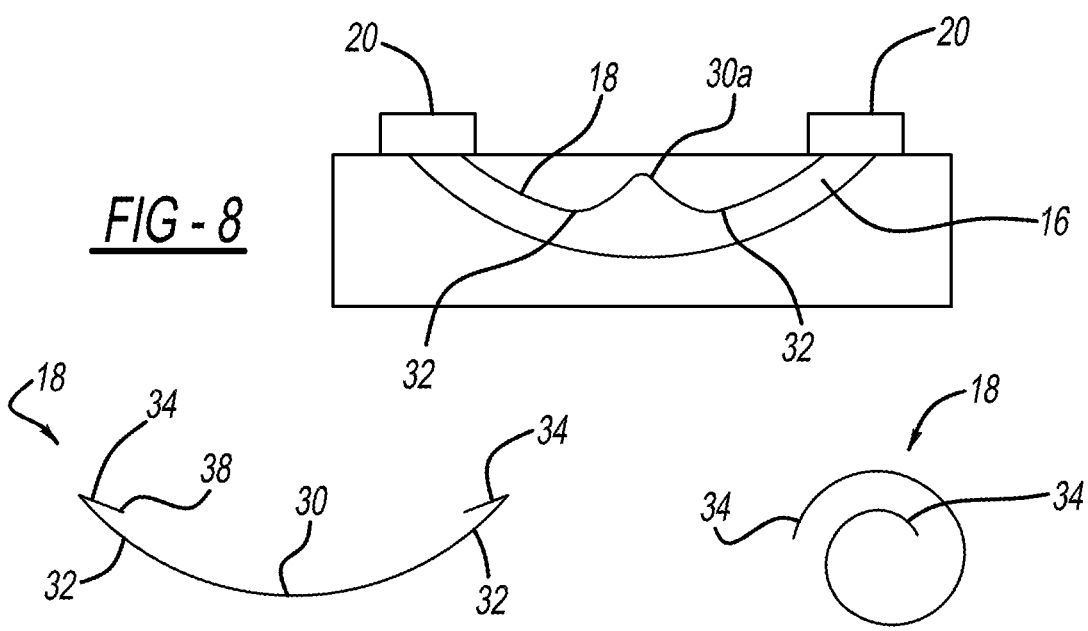
FIG - 9
FIG - 10

STAPLING DEVICE AND METHOD

CROSS REFERENCE TO RELATED APPLICATIONS

This application claims the benefit of U.S. Provisional Application No. 62/011,839 filed on Jun. 13, 2014, the entire contents of which is hereby incorporated by reference.

FIELD OF THE INVENTION

The present invention relates generally to visceral stapes for closing perforations in tissue.

BACKGROUND OF THE INVENTION

Perforations in the walls of internal organs and vessels may be naturally occurring, or formed intentionally or unintentionally. In order to permanently close these perforations and allow the tissue to properly heal, numerous medical devices and methods have been developed employing sutures, adhesives, clips, and the like. One class of such devices is commonly referred to as suture staples, surgical staples, or visceral staples. In certain applications, the staples hold the edges of a perforation together. Visceral staples have been successfully used in closing perforations, but are not without their drawbacks.

For example, one type of visceral staple is used with a suture to draw the staples together. When a series of staples are placed around a perforation, all of the individual sutures connected to the staples must be collected and connected together. It can often be difficult to properly tension each of the individual sutures to ensure proper approximation of the tissue around the perforation and complete closure thereof. This is especially critical within the gastrointestinal tract, where the travel of bacteria-laden fluids outside of the tract may cause unwanted and sometimes deadly infection. Moreover, many staple delivery devices are bulky or are otherwise difficult to use in endoscopic and laparoscopic procedures.

BRIEF SUMMARY OF THE INVENTION

The present invention provides medical devices and related methods for closing a perforation in a bodily wall in a manner that is simple and reliable, while at the same time gives increased versatility and control over perforation closure. One embodiment of a medical device, constructed in accordance with the teachings of the present invention, generally comprises a stapling device including an introducer member having an elongate base and defining a longitudinal axis therealong and a recess defined by the base, wherein the recess extends in a direction transverse to the longitudinal axis and is configured for holding a staple therein. The stapling device further includes a staple disposed within the recess in a delivery state, wherein the staple is biased toward a deployed state. The staple is held in place by a holding mechanism having a holding surface moveable between an engaged position and a disengaged position, the engaged position having the holding surface in contact with the staple in the delivery state, the disengaged position having the holding surface moved away from the staple such that the staple is free to transition toward the deployed state.

Another embodiment, in accordance with the teachings of the present invention, provides a method for attaching a visceral staple using the above described device. The method includes the steps of aligning the introducer member such that the recess and the staple disposed therein are arranged adjacent the tissue to be stapled and moving the holding mechanism from the engaged position to the disengaged position to release the staple from its engagement with the holding mechanism. After moving the holding mechanism, the step of transitioning the staple from the delivery state to the deployed state and piercing the tissue with the staple can be performed.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 6 is a schematic top view of an alternative embodiment of the stapling device showing recesses that are arranged at different distances from each other;

FIG. 7 is a schematic cross-sectional end view of the stapling device illustrating a holding mechanism positioned over the staple to retain it in a delivery state within the recesses;

FIG. 8 is a schematic cross-sectional end view of the stapling device illustrating an alternative delivery state of the staple;

FIG. 9 is a schematic view of a staple in its delivery state, the staple having a middle portion, end portions, ends, and barbs disposed at the ends;

FIG. 10 is a schematic view of the staple in its deployed state;

DETAILED DESCRIPTION OF THE INVENTION

Figure 1:
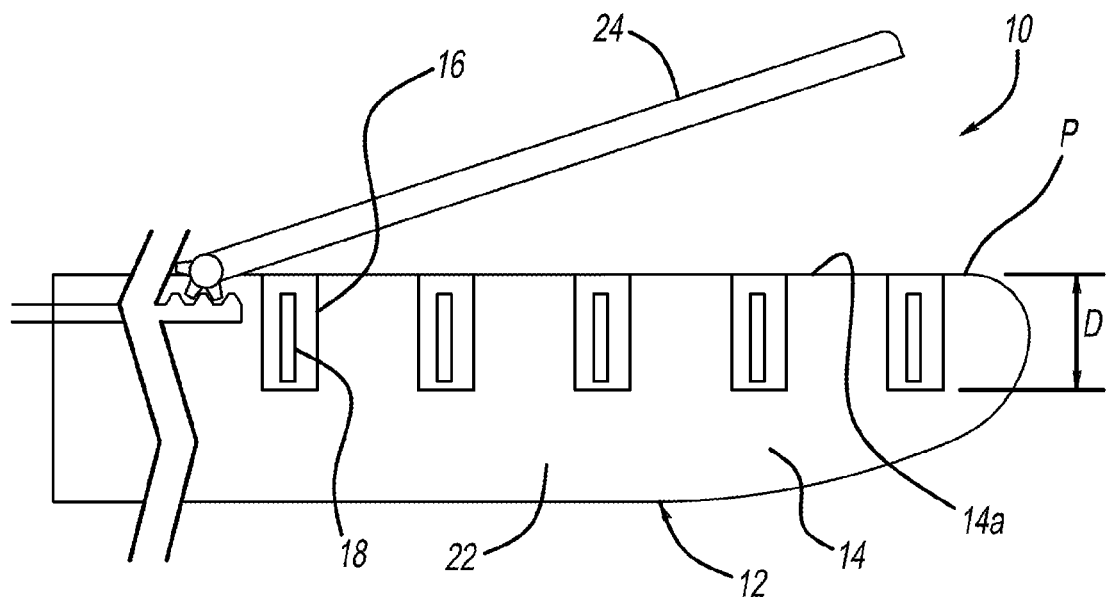
FIG. 1 is a schematic cross-section side view of a stapling device in accordance with the invention having a plurality of recesses with a staple disposed within the recesses.

Turning now to the figures, FIGS. 1-20 depict a device 10 for stapling visceral tissue. The device 10 generally includes an introducer member 12 that includes a base 14 defining a longitudinal axis A. The base 14 also defines a plurality of recesses 16 formed therein. The device 10 also includes a plurality of visceral staples 18 that are disposed within the recesses 16. The staples are held within the recesses by a holding mechanism 20 that is moveable between an engaged position and a disengaged position. The holding mechanism 20 includes a holding surface 20a against that is in contact with the staples 18 when they are in an engaged position in a delivery state.

With reference again to FIG. 1, the introducer member 12 has a proximal end 12a and a distal end 12b, with the longitudinal axis A extending therebetween. The base 14 of the introducer member can be in the form of a lower jaw 22 and an upper jaw 24. The lower jaw 22 preferably incudes the recesses 16 formed therein. However, in another approach, the recesses 16 can be formed in the upper jaw 24. The upper jaw is moveably mounted to the lower jaw 22, such that the jaws 22 and 24 can be opened and closed relative to each other. In a preferred form, the upper jaw 24 will generally pivot away from the lower jaw 22. The jaws 22 and 24 can be opened and closed to perform a clamping action in order to grasp tissue therebetween. In this approach, the holding mechanism 20 can be said to include the upper jaw 24 and lower jaw 22.

Figure 3:
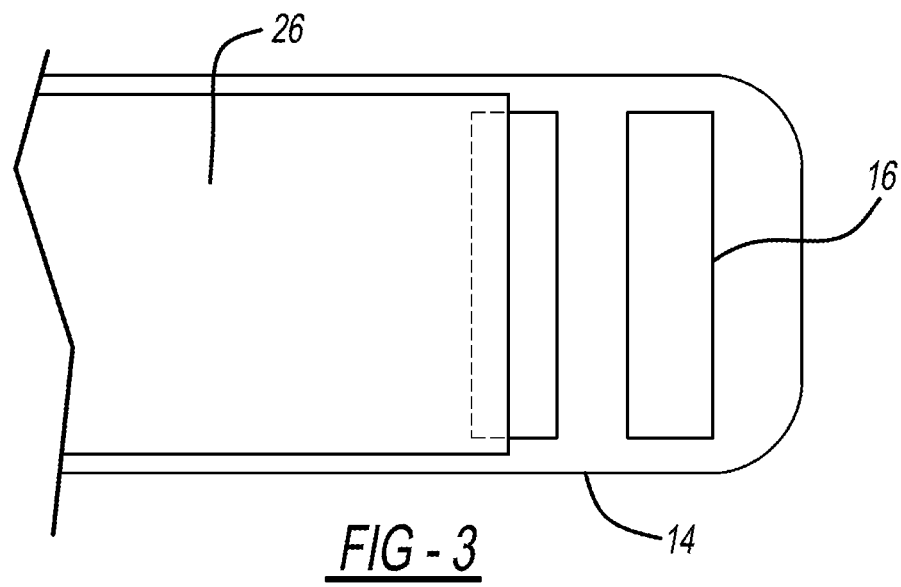
FIG. 3 is a schematic top view of the stapling device having a slidable cover.

In another form, the device 10 can include a lid 26 slidably attached to the base 14, as shown in FIG. 3. In this approach, the upper and lower jaws 22, 24 would not be used. Unless otherwise noted, references to the base 14 and lower jaw 24 can be interchangeable. As further described below, the recesses 16 are formed in the base 14, and the lid 26 or upper jaw 24 will cover the recesses 16 in the delivery state of the device 10.

Figure 4:
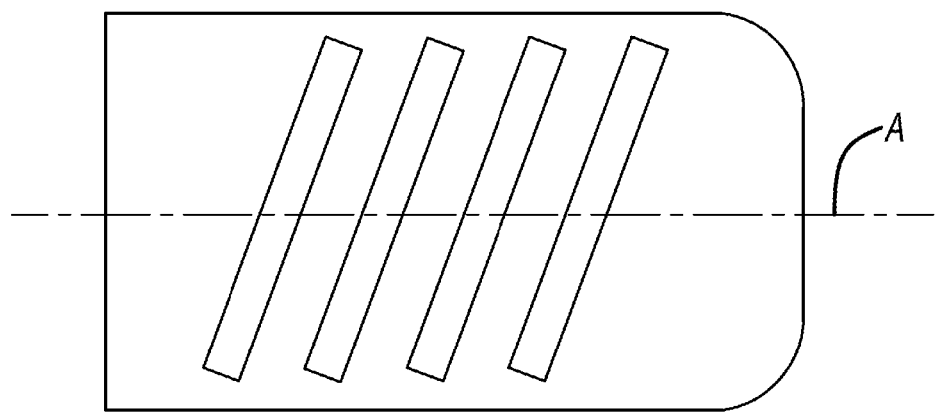
FIG. 4 is a schematic top view of an alternative embodiment of the stapling device showing recesses that are aligned at an oblique angle to the longitudinal axis.

With reference again to FIG. 1, the recesses 16 that are formed in the base can 14 can have a generally slot-like shape. In one form, the recesses can extend across the longitudinal axis A such that they extend generally perpendicular to the axis A. In another form, the recesses can extend at an oblique angle to the axis A, as shown in FIG. 4. In either case, the recesses 16 preferably extend transverse to the axis A. However, in another example, the recesses 16 could be aligned parallel to or at other orientations relative to the axis A.

Figure 2:
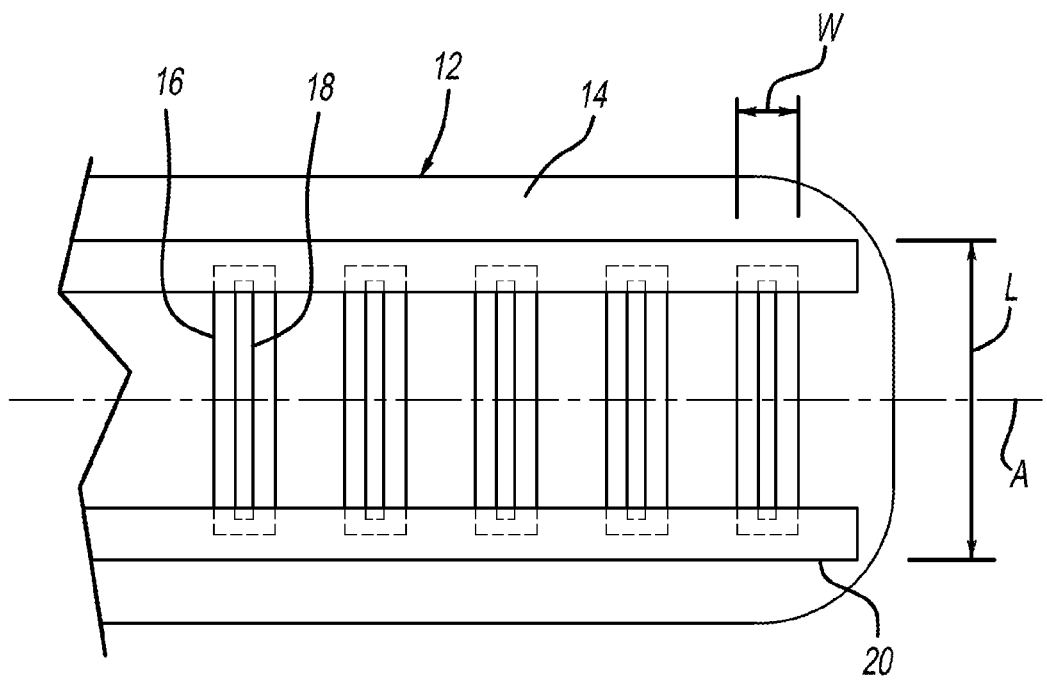
FIG. 2 is a schematic top view of the stapling device.
Figure 5:
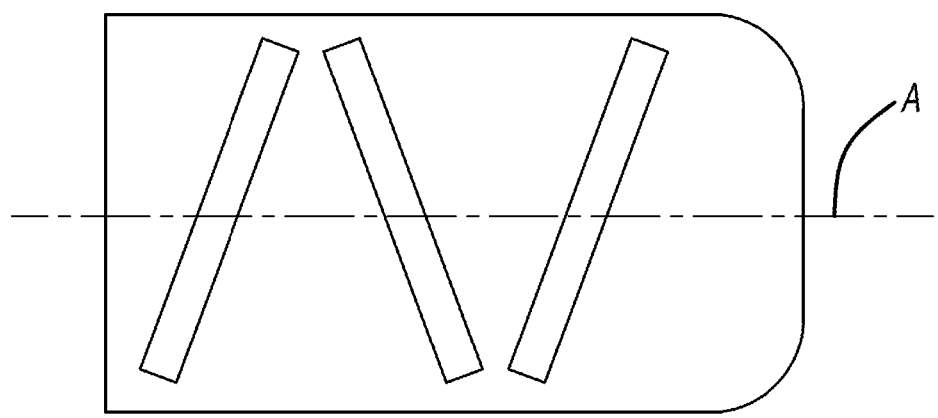
FIG. 5 is a schematic top view of an alternative embodiment of the stapling device showing recesses that are arranged in a zig-zag pattern.

The recesses 16 can be aligned relative to each other in a parallel configuration, as shown in FIGS. 1 and 2. In another approach, the recesses can be arranged at an angle relative to each other, such that they define a generally "zig-zag" configuration, as shown in FIG. 5.

The recesses 16 can also be arranged having a generally even spacing between each other. However, the spacing between the recesses 16 can also be different from recess to recess, such that spacing is uneven, as shown in FIG. 6. For example, the spacing between recesses 16 could decrease in a first direction along the axis A. Or, the spacing between the recesses 16 could increase in the first direction along the axis A. In another approach, the spacing could increase and then decrease (FIG. 6). The described variable spacing generally applies to recesses 16 that are arranged generally parallel to each other. Similarly, for recesses that arranged at an angle relative to each other, the angle between recesses can increase, decrease, or both increase and decrease in a first direction along axis A.

As described above, the recesses 16 have a generally slot-like shape. Thus, the recesses can have a depth D (FIG. 1), a length L (FIG. 2) that extends across the axis A, and a width W (FIG. 2) that generally extends in the same general direction as the axis A. The length is preferably greater than the width and the depth. Of course, other slot-like shapes can be used.

The depth of the recesses 16 can be generally constant, such that the recess 16 has a generally flat floor (FIG. 7). In another form, the depth can vary, such that recess is deeper at a middle point located near the axis A and shallower at the ends of the recess 16, such that the recess 16 has a generally curved cross-section (FIG. 8).

Each of the staples 18 are received in the recesses 16 such that the staples 18 can be delivered via the introducer member 12. With reference to FIG. 9, the staples 18 have a middle portion 30 and end portions 32 extending from each side of the middle portion 30. The end portions 32 define ends 34. The staples 18 are configured to be biased toward a deployed state (FIG. 10), and are bendable into a delivery state (FIGS. 7 and 8). In this regard, the staples 18 can be described as being resilient, such that bending them or arranging them in a position other than the deployed state will create a potential energy therein that will urge them toward the deployed state upon release. Once the staples 18 are freed from their delivery state, they will return to their deployed state.

The staples 18 and recesses 16 are shown in FIGS. 1 and 2 with one staple 18 being disposed within one recess 16. It will be appreciated, however, that the recesses 16 can also contain more than staple 18. For example, in one approach, a pair of staples 18 are disposed within one or more of the recesses 16. In another approach, three staples 18 are disposed within one or more recesses. Of course, other quantities of the staples 18 could also be disposed within one or more recesses 16. Similarly, one of the recesses 16 could contain one quantity of staples 18, while other recesses 16 could contain a different quantity of staples 18.

Each staple 18 is preferably formed of a material such as stainless steel, titanium, nitinol or other metals/alloys, although various ceramics or plastics can be employed, such as polycarbonates (PC), polyamides including Nylon(TM), polytetrafluorethylenes (i.e. PTFE and EPTFE), polyethylene ether ketones (PEEK), polyvinylchlorides (PVC), polyimides, polyurethanes, and polyethylenes (high, medium or low density), including multi-layer or single layer constructions with or without reinforcement wires, coils or filaments.

The staples 18 are bent and positioned within the recesses 16 in the delivery state. The staples are preferably bent such that permanent deformation of the staple 18 is avoided.

With reference to FIG. 10, the deployed state of the staple 18 is preferably in the form of a circular or other rounded shape, such as an oval. In this form, the ends 34 and at least a portion of the end portions 32 will preferably overlap to define a generally closed loop. In this approach, the ends 34 of the staple 18 will move toward each other from the delivery state to the deployed state once released. It will be appreciated that references to a closed loop refer to the overlapping configuration, and are not intended to indicate that the end portions 32 necessarily contact each. Of course, in this approach, the end portions 32 can still ultimately contact each other in the deployed state. In another approach, the end portions 32 may not overlap, such that the staple does not define a closed loop, but forms a partial loop. The ultimate deployment shape of the staple 18 can depend on the tissue through which the staple 18 is deployed, or a predefined shape.

As shown in FIG. 9, the staples 18 can also include barbs 38 disposed at the ends 34. The barbs 38 can be any known barb shape or type that allows for the ends 34 of the staple 18 to pierce through the tissue during the stapling process. The barbs 38 will preferably limit the ability of the staple 18 to be pulled back through the opening created by the piercing, thereby helping to maintain the stapled configuration of the tissue.

The holding mechanism 20, further described below, will retain the staples 18 in their delivery state until it is desirable to release the staples 18 from the introducer member 12. In this regard, the staples 18 can be selectively released by manipulating the holding mechanism 20. Prior to being released from the introducer member 12, the staples 18 are held retained in the delivery state, described above.

The staples 18 can be held in multiple delivery states. The delivery state is one where the staples 18 are bent into an extended or open shape, such as those shown in FIGS. 7 and 8, such that potential energy is created therein that will tend to urge the staple 18 toward the deployed generally circular configuration described above.

One type of delivery state for the staples 18 is shown in FIG. 7. In this configuration, the staples 18 have a generally arcuate shape, with a concave shape directed upward out of the recesses 16, and a convex shape directed downward into the recesses 16 in the delivery state. The staples 18 are stretched and opened relative to the looped deployed state. The holding mechanism 20 retains the ends 34 to limit the staple 18 from deploying toward its deployed state. The bias of the staple 18 is directed upward through the ends 34 against the holding mechanism 20, so the middle portion 30 of the staple may, in some cases, be exposed or uncovered by the holding mechanism 20. This particular delivery state has a generally wide and flat profile relative to the looped deployed state.

Another type of delivery state is shown in FIG. 8. In this configuration, the staple has a generally complex curvature having a serpentine profile, bowed, or humped shape. In this configuration, the middle portion 30 defines a hump 30a, and the end portions 32 extend from either side of the hump. The end portions 32 have a concave shape directed upward out of the recess 16, with the middle portion 30 having a convex shape directed upward out of the recess 16. The middle portion 30 has a concave shape directed downward into the recess 16, and the end portions 32 have convex shapes directed downward. The bias of the staple 18 is directed upward through the ends 34 against the holding mechanism 20, so the middle portion 30 of the staple can, in some cases, be exposed or uncovered by the holding mechanism 20. This particular delivery state can have a generally narrower and taller profile relative to the delivery state previously described, depending on the size of the recess 16. Alternatively, a longer staple 18 can be used in a similarly sized recess 16. This is due to the staple 18 having the hump shape. The width of the staple 18 is compressed laterally, thereby causing the hump shape of the middle portion 30. The height of the middle portion 30 in this arrangement can vary depending on the amount of lateral compression in the staple 18.

Regardless of the delivery state used, the staple 18 is altered from its deployed loop shape, such that there is a bias in the staple 18 that is opposed and held by the holding mechanism 20. The staple 18 is deployed and allowed to transition into its deployed state by releasing at least one of its ends 34 from its engagement with the holding mechanism 20.

The holding mechanism 20, as briefly described above, acts to retain, or hold, the staples 18 in place within the introducer member 12 during delivery of the introducer member 12 to the target site for stapling. The holding mechanism 20 can have different configurations or arrangements depending on the needs of the user.

Figure 11A:
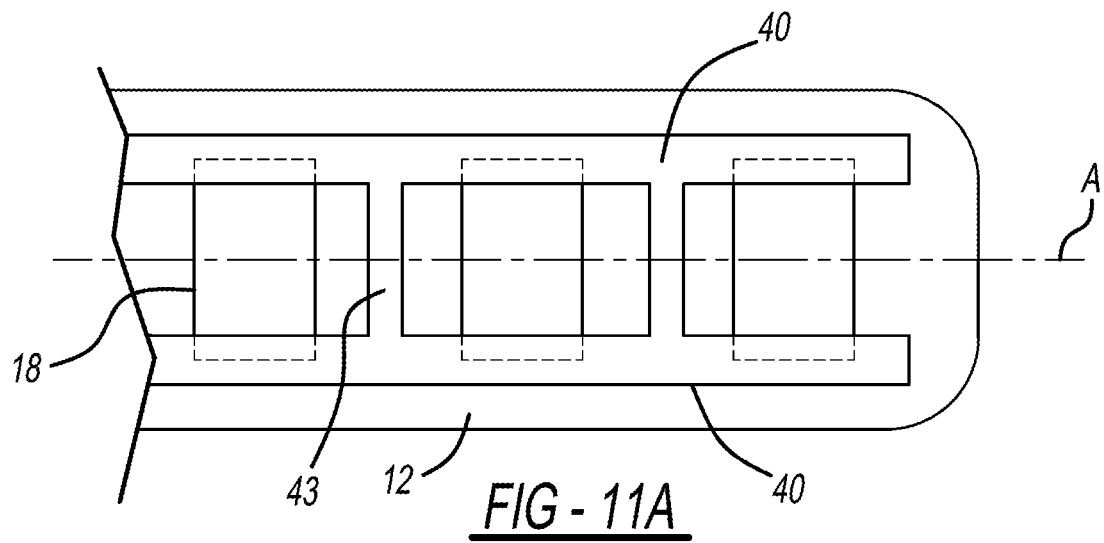
FIG. 11A is a schematic top view of a holding mechanism having a pair of rails.
Figure 12:
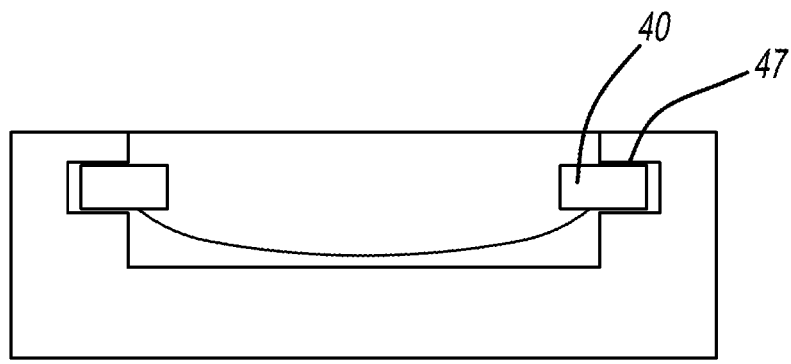
FIG. 12 is a schematic cross-sectional end view illustrating the holding mechanism.

As shown in FIG. 11A, in one approach the holding surface 20a of the mechanism 20 can be in the form of a pair of rails 40. The rails 40 each have a generally elongate shape that extends generally parallel to the longitudinal axis A of the introducer member 12. The rails 40 are slidably coupled to the introducer member 12 to allow the rails 40 to be retracted relative to the introducer member 12 while maintaining a desired position of the introducer member 12 and the staples 18 disposed therein. In one form, as shown in FIG. 12, the rails 40 can be disposed within a channel 42 formed in the introducer member 12. The channel 42 will generally extend longitudinally and correspond to the shape of the rails 40, such that the rails 40 can slide within the channel 42. The channel 42 will also hold the rails 40 in place so that the biasing force exerted by the staples 18 will not overcome the rails 40 that are positioned above the staples 18. However, it will be appreciated that the rails 40 can be slidably coupled to introducer member 12 in other approaches without the use of the channel 42. For example, the rails 40 could be disposed on the surface of the introducer member 12 with a protrusion extending into a surface groove of the introducer member, or the like.

Figure 11B:
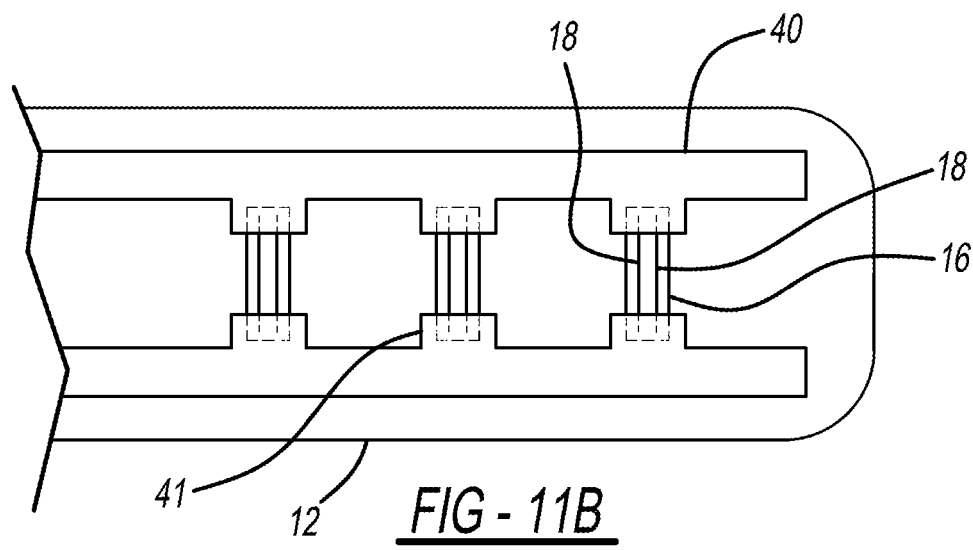
FIG. 11B is a schematic top view of a holding mechanism having a pair of rails and tabs extending inwardly from the rails.

With reference to FIG. 11B, in one approach the rails 40 include tabs 41 extending laterally across the introducer member. The tabs 41 are aligned with the recesses 16 to retain the staples 18 therein. The tabs 41 are, accordingly, spaced apart at a similar spacing as the recesses 16. When the rails 40 are retracted, the tabs 41 will move to expose the staples 18, allowing to extend out of the recesses 16. Due to the tabs 41 being spaced apart, when retracted, each of the tabs 41 will move to an area longitudinally adjacent the recesses 16 generally simultaneously. This coordinated movement of each of the tabs 41 will allow each of the staples 18 to extend from the recesses 16 at approximately the same time, rather than sequentially as in the case of a rail 40 without tabs 41.

The rails 40 can be independently moveable relative to each other, such that one of the rails 40 can be retracted while the other one remains in place. This would result in one side of the staple 18 becoming free and would allow the staple 18 to transition into the its deployed state from the side of the introducer member 12 where the rail 40 was retracted.

The rails 40, while independently moveable, could also be retracted at approximately the same rate such that the ends 34 of the staple 18 are released at approximately the same time.

In another approach, the rails 40 can be coupled to each other via lateral supports 43 (FIG. 11) that connect the rails 40 together. In this approach, the rails 40 will be retracted at about the same rate due to the coupling. The supports 43 can extend laterally and perpendicular to the rails 40, or they can extend at an oblique angle to the rails 40. The rails 40 can be coupled via one support 43 or multiple supports 43. The supports 43 can be attached to the rails 40 via an adhesive, welding, or other known attachment methods known in the art. In another form, the rails 40 and supports 43 can be formed as a unitary, integral, or monolithic structure.

Figure 13:
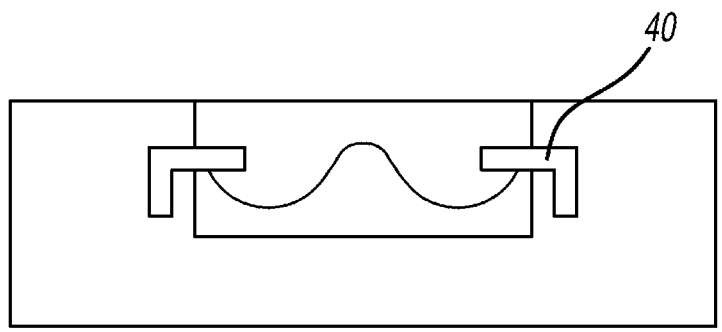
FIG. 13 is a schematic cross-sectional end view illustrating a holding mechanism having L shaped rails and showing the staple in an alternative delivery state.
Figure 14:
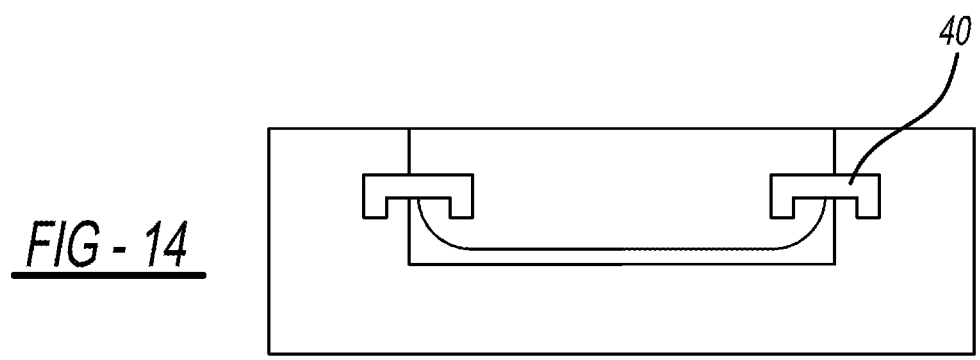
FIG. 14 is a schematic cross-sectional end view illustrating a holding mechanism having U shaped rails.

The rails 40 can have various cross-sections that can be used to retain the ends 34 of the staples 18. With reference to FIG. 12, in one form, the rails 40 can have a generally rectangular of flat cross-sectional profile. In another form, as shown in FIG. 13, the rails 40 can have an "L" shaped cross-section, or single-bend shape. In another form, the rails can have a "U" shaped cross-section, shown in FIG. 14. In yet another form, the rails 40 can have a curved shape. Other shapes could also be used to retain the staples 18. The rails 40 can have any shape that will allow for the ends 34 of the staples 18 to be positioned below the rails 40 such that the bias in the staple 18 is opposed by a portion of the rail 40 disposed above the ends 34. The rails 40 do not have to be of matching style and shape. Different rail shapes could be combined, such as using an L shaped rail with a U shaped rail, if desired.

Figure 15:
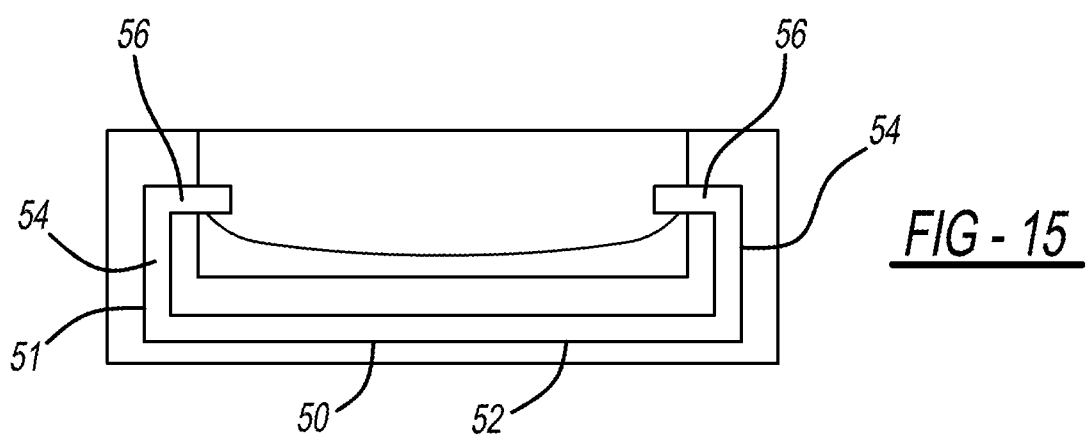
FIG. 15 is a schematic cross-sectional end view illustrating a holding mechanism in the form of a monorail.

With reference to FIG. 15, in another approach, the holding mechanism 20 is in the form of a single structure, or monorail 50, that extends longitudinally parallel to the axis A of the introducer member 12. Similar to the rails 40, the monorail 50 is slidable relative to the introducer member 12. The monorail 50 is disposed within a channel 52 formed in the introducer member 12, where the channel 52 is sized to generally correspond to the shape of the monorail 50 such that the monorail can slide longitudinally therealong.

The monorail 50 is preferably formed as a single monolithic structure, having a base portion 52 and two end portions 54 that extend from the base portion 52. The base portion 52 could also be referred to as a middle portion, as it is in the lateral middle of the monorail 50. The base portion 52 can have a generally flat shape that extends laterally across the introducer member 12, or it can have a curved shape having a concave or convex curvature, or a complex curvature.

The end portions 54 extend away from the base portion 52, and transition into a laterally inward facing portion. In this regard, the end portions 54 generally bend upward and then inward toward the axis A. The end portions 54 thereby define a shelf portion 56 that retains the ends 34 of the staple 18, in a manner similar to the rails 40 described above. As shown in FIG. 15, the monorail can have a generally rectangular cross-sectional profile. In another form, the transition from the base portion 52 to the end portions 54 and shelf portion 56 can be generally curved, such that the end portions 54 have a concave shape facing toward the longitudinal axis and a convex shape facing outwardly.

The monorail 50 can be retracted, similar to the rails 40, to release the staples 18 in sequence. Unlike independently moveable rails 40, but similar to rails 40 that are linked together, the monorail 50 will release both ends 34 of the staple 18 at approximately the same time.

Figure 16:
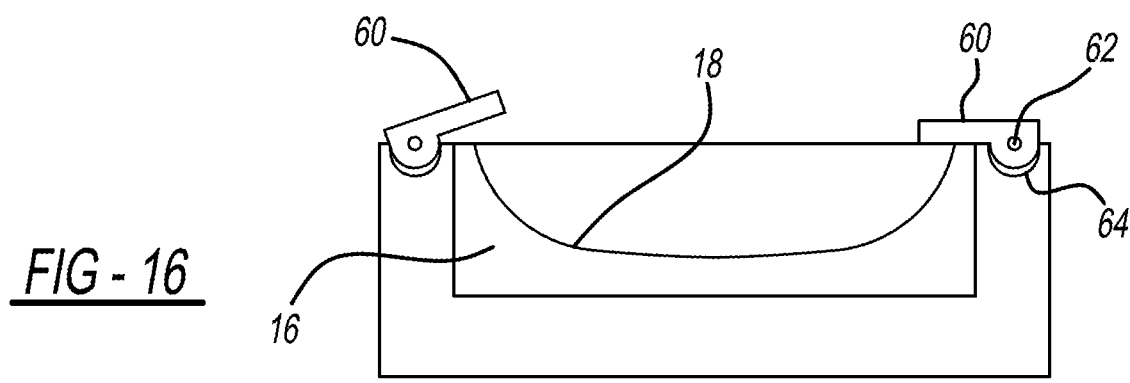
FIG. 16 is a schematic cross-sectional end view illustrating a holding mechanism in the form of pivotable flaps.
Figure 17:
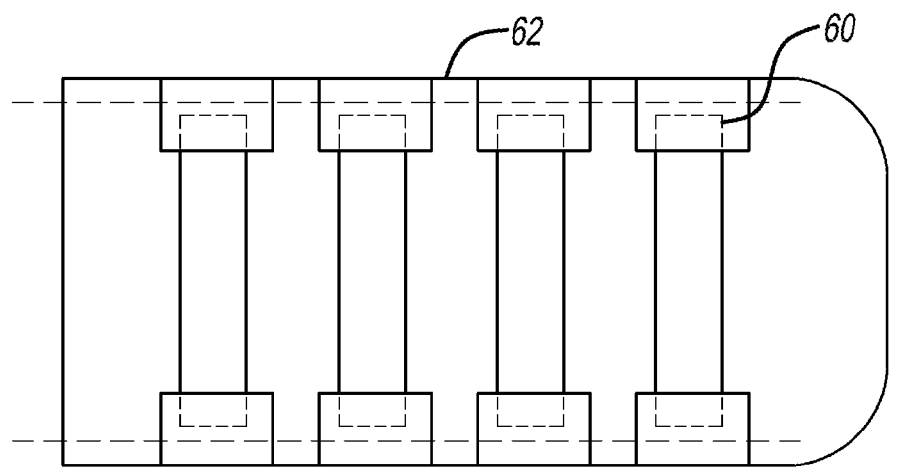
FIG. 17 is a schematic top view illustrating the pivotable flaps in the form of individual flaps for each recess and staple.

With reference to FIGS. 16-17, the holding surface 20a of the holding mechanism 20 can be in the form a pivotable flap 60. The flap 60 can be pivotally coupled to the introducer member 12 at the outer edges of the recesses 16, such that the flap 60 extends over the ends 34 of the staple 18 disposed within the recess 16, similar to how the rails 40 extend over the staple 18 to retain the staple 18 in the delivery state.

The flaps 60 can be biased open, such as by using a spring bias or by being formed to be resiliently biased toward an open state. The flaps 60 can be held closed by a trigger wire 62 extending through a channel 64 formed in the introducer member 12 and through the flaps 60. More particularly, each of the flaps 60 can include a protrusion that defines a through-hole, and the wire 62 extends through the through-hole to retain the flap 60. To release the flaps 60, thereby releasing the staples 18 being retained by the flaps 60, the trigger wire 62 can be retracted, allowing the flaps 60 to open according to their bias. With the flaps 60 open, the staples 18 are free to transition into the deployed state, as described previously above.

Similar to the rails 40, a pair of trigger wires 62 can be used and retracted independently of each other to release one side of the staple 18 prior to the other side of the staple 18. Alternatively, the wires 62 can be retracted at the same rate, or simultaneously, to release both sides of an individual staple 18 at the same time. Similar to the rails 40 and monorail 50, the flaps 60 and trigger wire 62 arrangement will release the staples 18 sequentially.

Figure 18:
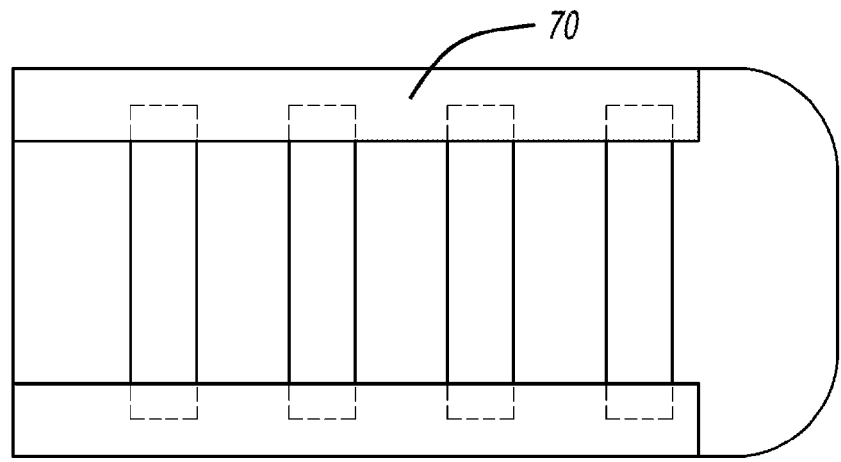
FIG. 18 is a schematic top view illustrating the pivotable flaps in the form of a single flap for each side of the stapling device that retains multiple staples.

In another form, as shown in FIG. 18 one or more large flaps 70 can be disposed on each side of the introducer member 12. In this form, the large flap can retain more than one staple 18. The large flap 70 can be released in a similar manner to the flaps 60, by releasing a trigger wire or other retaining mechanism, thereby allowing the staples 18 being retained by the large flap 70 to be released. The flaps 70 on opposite sides of the introducer member 12 can be released one after the other or simultaneously, depending on the needs of the user. It will be appreciated that flaps having other lengths can also be used, such as flaps that retain more than one but less than all of the staples 18 of a particular device.

As described previously, the staples 18 are configured to be biased toward a generally looped shape when freed from being retained by the holding mechanism 20. In this regard, the staples 18 will tend to extend out of the compressed shape that they have while being disposed within the recesses 16. Thus, the staples 18 will generally rise out of the recesses when deployed.

The introducer member 12 can be in the form of a lower jaw 22 and an upper jaw 24, as described above. In one approach, the upper jaw 24 is pivoted open, thereby presenting the staples 18 disposed within the recesses 16 for deployment. In a similar manner, the slidable cover 26 can be retracted to similarly expose the staples 18 for deployment. This type of presentation of the staples 18 can be particular beneficial for instances where the introducer member 12 can be pressed against a tissue surface along the tissue perforation.

In this approach, the staples 18 can be released in the manners described above with respect to the various holding mechanisms. The staples 18 will move toward their looped deployed state, piercing the adjacent tissue and becoming lodged therein, closing the perforation in the tissue.

In another approach, the upper and lower jaws 22, 24 can be used as a clamp to grasp tissue T therebetween. In this approach, the clamping performed by the introducer device 12 will preferably remain in a clamped position when the staples 18 are deployed from recesses 16.

In this approach, then, the staples 18 will preferably have an open region adjacent and above the recesses 16 so that the staples 18 can move out of the recesses 16 and into their looped deployed state. To accommodate this, and with reference to FIGS. 19-21, the upper jaw 24 can define a plurality of cavities 80 that correspond generally to the locations and size of the recesses 16 defined by the lower jaw. In another approach, the upper jaw can define a single cavity 82 that extends over the plurality of recesses 16. In either case, the cavities 80 or cavity 82 will allow the staples 18 to extend out of the recesses and through the tissue that is clamped between the upper and lower jaws 22, 24. However, it will be appreciated that the staples 18 could also be deployed from the recesses 16 while clamped even in the absence of a cavity disposed adjacent and above thereto. The tissue being clamped can provide enough space between the upper and lower jaws 22, 24 such that the staples 18 can pierce through the tissue T clamped therebetween.

Thus, with reference to the above, the stapling device 10 defines an upper surface 14*a* of the base 14. The recess or recesses 16 open upwardly through the upper surface 14*a* of the base 14. The upper surface 14*a* defines an engagement plane P (shown in FIG. 1). The tissue T is generally held against the engagement plane P for deploying the staple or staples 18 through the plane P and tissue T. As described above, the recess or recesses 16 are sized and positioned relative to the staple 18 such that as the staple 18 transitions from the delivery state to the deployed state upon being released by the holding mechanism 20, the ends 34 of the staple 18 pass through the engagement plane P and the tissue T to thereby staple the tissue T.

In another aspect of the device 10, the device 10 can include a vacuum channel 90 (shown in FIG. 7) defined by the base 14. The vacuum channel 90 extends through the base 14 and is in fluid communication with the recess or recesses 16. The vacuum channel 90 is also configured for attachment to the vacuum or negative pressure source (not shown) that can create a reduced pressure state in the channel 90. By reducing the pressure in the channel 90, and in turn the recess or recesses 16, tissue T adjacent the base 14 and, more particularly, located over the recess or recesses 16 will be pulled or drawn toward the recess or recesses 16. In some cases, the tissue T may be drawn into the recess recesses 16. This approach can assist in the stapling process that is further described below by helping to keep the tissue T in contact with the base 14 when the staples 18 are transitioning from the delivery state to the deployed state.

Having the described the structure of the stapling device 10 above, a method for using the stapling device 10 will now be described.

The stapling device 10 is introduced into the body and toward a target location using known methods appropriate for the target location. The introducer member 12 is positioned adjacent the body tissue to be stapled. The staples 18 are housed within the recesses 16 and held in place via the holding surface 20*a* of the holding mechanism 20. This introduction of the stapling device 10 with the staples 18 held within the recesses 16 is referred to as the delivery state. In the delivery state, the staples 18 can be covered and shielded from contact with body tissue by the upper jaw 24 or the cover 26.

With the introducer member 12 position at the desired location, the staples 18 can be exposed and presented for stapling. This can be accomplished by pivoting open the upper jaw 24 or by retracting the slidable cover 26.

Figure 19:
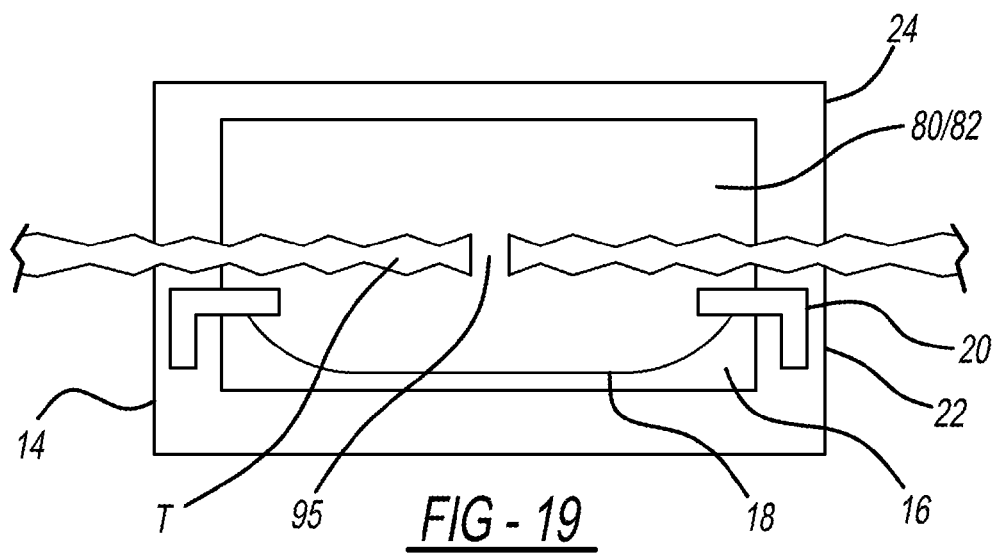
FIG. 19 is a schematic cross-sectional end view of the stapling device having upper and lower jaws and having tissue clamped therebetween and illustrating an initial position of a method of employing the stapling device.

With reference to FIG. 19, the staples 18 are aligned over an opening or seam 95 in the body tissue T that is intended to be stapled, and the base member 14 is positioned adjacent the opening or seam 95 with at least a portion of the staples 18 spanning the opening or seam 95 in the tissue T. In a preferred approach, the base member 14 is pressed against the tissue T such that the engagement plane P contacts the tissue T.

Figure 20:
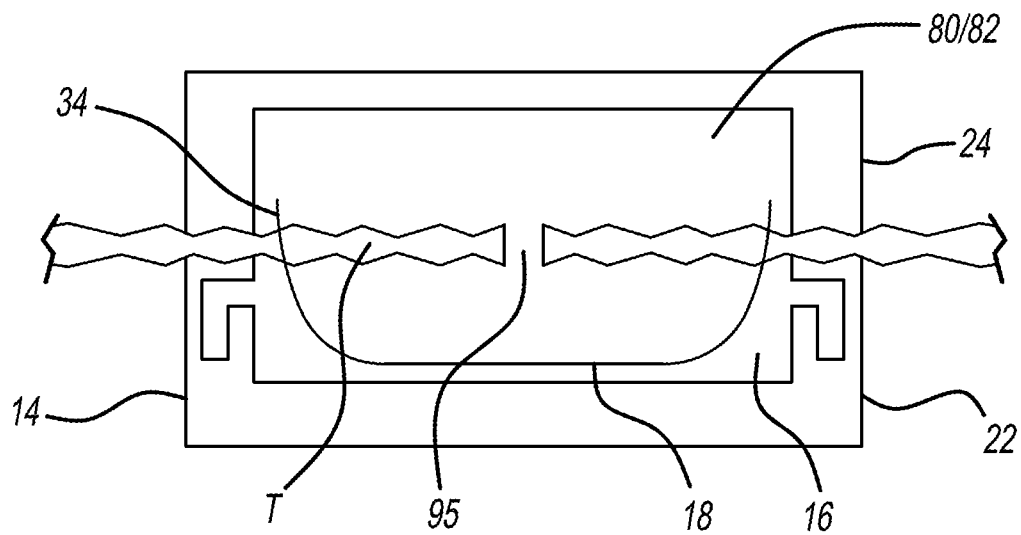
FIG. 20 is a schematic cross-sectional end view of the stapling device showing the staple initially piercing the tissue and illustrating an further position of a method of employing the stapling device.

As shown in FIG. 20, with the staples 18 in position for deployment into the tissue, the holding mechanism 20 is released from its engagement with at least one of the staples 18. The staple 18, upon being released, will transition toward its closed loop state due to the bias or other shape memory characteristics of the staple 18. It will be appreciated that references to bias or shape-memory can be used interchangeable herein or generally referred to as a biased state, and refers to the staple characteristic of being loaded such that it will transition from its delivery state to its deployed state upon being released. Of course, once in the deployed state, the staple 18 will tend to remain biased toward its deployed state to maintain the closed condition of the staple 18. During this transition, at least one end 34 of the staple 18 will pierce through the tissue T on at least one side of the seam 95. The end 34 will either continue through the tissue on the opposite side of the seam, or the opposite end 34 will pierce through the opposite side of the tissue. The staple 18 will end its transition in its generally closed deployed state. As stated above, the closed deployed state can include an overlap of the ends 34, or the ends 34 could be non-overlapped. In either case, the ends 34 move toward each other upon being released.

Figure 21:
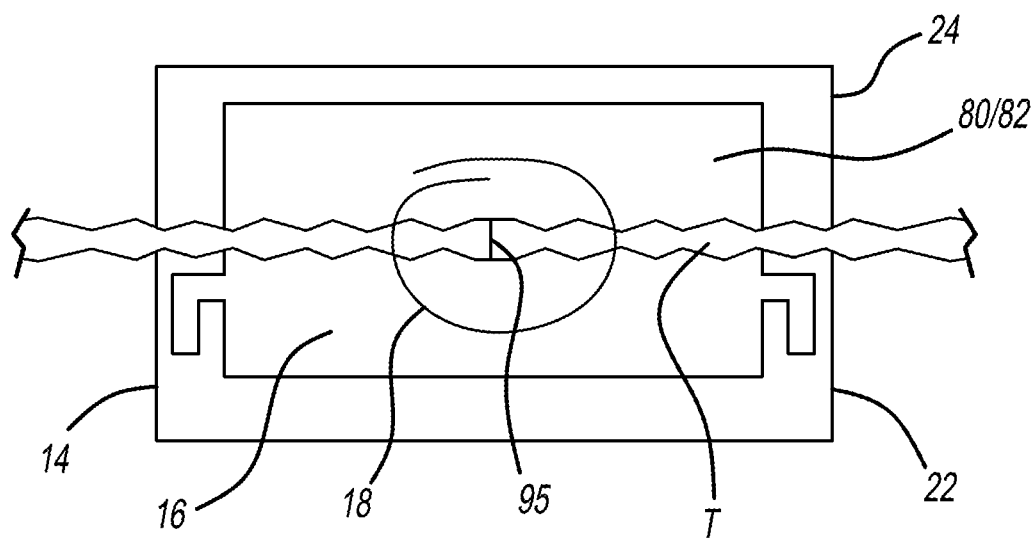
FIG. 21 is a schematic cross-sectional end view of the stapling device in its fully deployed state stapling the tissue and illustrating a further position of a method of employing the stapling device.

After being released, and after initially piercing the tissue T, the staples 18 will continue to transition toward the deployed state, as shown in FIG. 21. With the staples 18 in the deployed state, the tissue T can be drawn together, closing the opening or seam 95.

Accordingly, as shown in FIGS. 19-21 and described above, when the staples 18 are allowed to close after being released, the tissue T will be drawn closer together corresponding to the changing shape of the staples 18. Drawing the tissue T closer together will close the incision or wound or opening that the staples 18 are intended to close. As shown in FIGS. 19 and 20, the seam 95 is shown as opening between two portions of the tissue T, and FIG. 21 shows the portions of the tissue T being pushed against each other to close the seam 95.

As described above, the stapling device 10 can include upper and lower jaws 22, 24. In this approach, the upper and lower jaws 22, 24 can clamp the tissue T to be stapled prior to releasing the staples 18. An illustration of the tissue T being clamped between the upper and lower jaws 22, 24 can be seen in FIGS. 19-21. With the tissue T clamped between the jaws 22, 24, the staples 18 can be released and allowed to pierce the tissue T as described above. It will be appreciated, however, that the described stapling method can be performed with devices 10 that do not perform the clamping step, and that FIGS. 19-21 illustrate the method having the jaws 22 and 24 being clamped. It will be understood that the method without clamping would not include the illustrated upper jaw 24.

Furthermore, the staples 18 can be released in different ways depending on the way in which they are retained. The staples 18 can be released sequentially by retracting the holding mechanism 20. In this approach, a first staple 18 can be released by retracting the holding mechanism 20 a first distance, and a second staple can be released by retracting the holding mechanism 20 a second distance. This can be repeated for additional staples.

The staples 18 can also be released at one end 34 before being released at the opposite end. One rail 40 of the holding mechanism 20 can be retracted, releasing the first end 34 of the staple. The opposite rail 40 can be subsequently retracted to release the opposite end 34 of the staple 18. This can be performed for one staple 18 or multiple staples 18 in succession.

In another form, the staples 18 can be released sequentially, as described above, by releasing the flaps 60. The flaps 60 can be released by retracting the trigger wire 62, on one side before the other or simultaneously, allowing the flaps 60 to open due to their bias.

In another approach, the staples 18 can all be released at approximately the same time by releasing the flaps 70, either on one side before the other or simultaneously.

The progression of the staples 18 from the delivery state shown in FIG. 19 and ultimately to the deployed state shown in FIG. 21 will operate similarly for each staple 18, regardless of whether the staples 18 are released sequentially or simultaneously. It will be appreciated the illustrated deployment shown in FIGS. 19-21 applies to each of the staples 18 that are ultimately deployed according the sequencing described above.

The above described staple release methods can be performed whether tissue is clamped between the jaws 22, 24 or if the base member 14 is located adjacent the tissue without the tissue being clamped.

After one or more staples 18 have been deployed, the stapling device 10 can be retracted from the body.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A device for stapling tissue, the device comprising:
an introducer member having an elongate base and defining a longitudinal axis extending in a proximal and distal direction therealong;
a recess defined by the base, wherein the recess extends in a direction transverse to the longitudinal axis and is configured for holding a staple therein, wherein the recess includes first and second outer ends on opposite sides of the longitudinal axis and the recess further includes a distal end and a proximal end, wherein the distal end and the proximal end are closed;
a staple disposed within the recess in a delivery state, wherein the staple, in the delivery state, is biased toward a deployed state; and
a holding mechanism having a holding surface moveable between an engaged position and a disengaged position, the engaged position having the holding surface in contact with the staple in the delivery state, the disengaged position having the holding surface moved away from the staple such that the staple is free to transition toward the deployed state;
wherein the staple has first and second ends, and the first and second ends are disposed inwardly from the first and second outer ends of the recess in the delivery state.

2. The device of claim 1, wherein the holding mechanism includes an upper jaw, and wherein the base of the introducer member includes a lower jaw, and wherein the upper jaw is moveably mounted to the lower jaw.

3. The device of claim 1, wherein the staple has first and second ends, a first outer portion disposed at the first end, a second outer portion disposed at the second end, and a middle portion connecting the first and second outer portions, wherein the first and second outer portions and the middle portion have a concave curvature facing out of the recess in the delivery state.

4. The device of claim 1, wherein the staple has first and second ends, a first outer portion disposed at the first end, a second outer portion disposed at the second end, and a middle portion connecting the first and second outer portions, wherein the first and second outer portions have a concave curvature facing out of the recess and the middle portion has a convex curvature facing out of the recess in the delivery state.

5. The device of claim 1, wherein the staple has first and second ends, a first outer portion disposed at the first end, a second outer portion disposed at the second end, and a middle portion connecting the first and second outer portions, wherein the first and second outer portions move toward each other as they transition from the delivery state to the deployed state.

6. The device of claim 1, wherein the holding surface of the holding mechanism is defined by a pair of longitudinally extending rails, wherein the rails are separate and moveable independently of each other.

7. The device of claim 1, wherein the holding surface of the holding mechanism is defined by a pair of longitudinally extending rails, wherein the rails are coupled together such that rails are moveable in unison.

8. The device of claim 1, wherein the holding mechanism is pivotable relative to the introducer member, wherein the holding mechanism comprises a plurality of pivotable flaps, wherein the pivotable flaps are biased toward an open position, wherein the pivotable flaps are retained in a closed position by a triggering mechanism.

9. The device of claim 1, wherein the holding mechanism comprises a pair of outer portions and a middle portion therebetween, wherein the outer portions have a concave structure as viewed from the longitudinal axis, and the respective concavities of the outer portions face each other.

10. The device of claim 1, wherein the holding mechanism comprises a pair of outer portions and a middle portion therebetween, wherein the outer portions are disposed both above and below first and second ends of the staple.

11. The device of claim 2, wherein the upper jaw and the lower jaw define a cavity therebetween when the jaws are in a closed position.

12. The device of claim 11, wherein the holding mechanism is disposed between the recess and the cavity.

13. The device of claim 1, wherein the recess opens upwardly through an upper surface of the base, the upper surface defining an engagement plane, and wherein the recess is sized and positioned relative to the staple such that as the staple transitions from the delivery state to the deployed state the ends of the staple pass through the engagement plane.

14. The device of claim 1 further comprising a vacuum channel extending through the base and in fluid communication with the recess, the vacuum channel configured for attachment to a vacuum source for reducing fluid pressure within the recess to pull tissue adjacent the base toward the recess.

15. A device for stapling tissue, the device comprising:
an introducer member having an elongate base and defining a longitudinal axis therealong;
a recess defined by the base, wherein the recess extends in a direction transverse to the longitudinal axis and is configured for holding a staple therein;

a staple disposed within the recess in a delivery state, wherein the staple, in the delivery state, is biased toward a deployed state;

a holding mechanism having a holding surface moveable between an engaged position and a disengaged position, the engaged position having the holding surface in contact with the staple in the delivery state, the disengaged position having the holding surface moved away from the staple such that the staple is free to transition toward the deployed state; and a plurality of recesses, each recess configured for holding a staple therein.

16. A method for attaching a visceral staple to body tissue, the method comprising:

delivering a stapling device to a target stapling location, the stapling device comprising:

an introducer member having an elongate base and defining a longitudinal axis extending in a proximal and distal direction therealong;

a recess defined by the base, wherein the recess extends in a direction transverse to the longitudinal axis and is configured for holding a staple therein, wherein the recess includes a distal end and a proximal end, wherein the distal end and the proximal end are closed;

a staple having first and second ends and disposed within the recess in a delivery state, wherein the staple, in the delivery state, is biased toward a deployed state, and the first and second ends are disposed within the recess in the delivery state; and a holding mechanism having a holding surface moveable between an engaged position and a disengaged position, the engaged position having the holding surface in contact with the staple in the delivery state, the disengaged position having the holding surface moved away from the staple such that the staple is free to transition toward the deployed state;

aligning the introducer member such that the recess and the staple disposed therein are arranged adjacent the tissue to be stapled;

moving the holding mechanism from the engaged position to the disengaged position to release the staple from its engagement with the holding surface of the holding mechanism;

transitioning the staple from the delivery state to the deployed state; and piercing the tissue with the staple.

17. The method of claim 16, wherein the step of moving the holding mechanism comprises retracting the holding mechanism proximally.

18. The method of claim 17, wherein the step of retracting the holding mechanism proximally comprises retracting the holding mechanism a first distance to release a first staple and retracting the holding mechanism a second distance to release a second staple.

19. The method of claim 16, wherein the step of moving the holding mechanism comprises pivoting the holding mechanism.

20. The method of claim 16 further comprising the step of clamping tissue between an upper jaw and lower jaw of the introducer member.

* * * * *